US 6,355,049 B1

(12) United States Patent
Gill

(10) Patent No.: US 6,355,049 B1
(45) Date of Patent: Mar. 12, 2002

(54) HEAD FIXATION APPARATUS

(75) Inventor: Steven Streatfield Gill, London (GB)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/489,580

(22) Filed: Jan. 21, 2000

Related U.S. Application Data

(63) Continuation of application No. 08/872,456, filed on Jun. 10, 1997, now abandoned, which is a continuation of application No. 08/639,324, filed on Apr. 25, 1996, now abandoned, which is a continuation of application No. 08/472,731, filed on Jun. 7, 1995, now abandoned, which is a continuation of application No. 08/283,921, filed on Aug. 1, 1994, now abandoned, which is a continuation of application No. 08/023,480, filed on Feb. 25, 1993, now abandoned, which is a continuation of application No. 07/911,351, filed on Jul. 8, 1992, now abandoned, which is a continuation of application No. 07/787,764, filed on Nov. 6, 1991, now abandoned, which is a continuation of application No. 07/673,858, filed on Mar. 21, 1991, now abandoned, which is a continuation of application No. 07/568,524, filed on Aug. 14, 1990, now abandoned, which is a continuation of application No. 07/278,270, filed on Nov. 30, 1988, now abandoned.

(30) Foreign Application Priority Data

Dec. 2, 1987 (GB) .............................. 8728150

(51) Int. Cl.$^7$ .............................................. A61B 19/00
(52) U.S. Cl. ........................................ 606/130; 5/622
(58) Field of Search .................... 606/130; 600/417; 378/195, 208; 5/622

(56) References Cited

U.S. PATENT DOCUMENTS 2,976,417 A * 3/1961 Freeman .................. 378/170
3,227,440 A    1/1966 Scott
3,514,606 A *  5/1970 Rabey ..................... 378/195
3,614,950 A * 10/1971 Rabey
3,777,124 A   12/1973 Pavkovich (List continued on next page.)

FOREIGN PATENT DOCUMENTS

| DE | 2809645 | 11/1978 |
| DE | 3508730 | 9/1986 |
| EP | 0 018 166 | 10/1980 |
| EP | 0 062 941 | 10/1982 |
| EP | 0146699 | 7/1985 |

(List continued on next page.)

OTHER PUBLICATIONS

Brown, Russell A., "A Stereotactic Head Frame for Use with CT Body Scanners", Investigative Radiology, vol. 14, No. 4, (Jul. –Aug. 1979).

Castleman Kenneth R., "Stereometric Ranging", Digital Image Processing, Prentice–Hall, Inc., Englewood Cliffs, New Jersey, 1979, pp. 364–369 (Chapter from a Book).

Fuchs, Henry et al., "Acquisition and Modeling of Human Body Form Data," SPIE, vol. 166, Applications of Human Biosteriometrics (NATO) (1978).

(List continued on next page.)

*Primary Examiner*—Michael H. Thaler

(57) ABSTRACT

A Head fixation apparatus includes a frame and a fixation structure for repeatably and reproducibly fixing the frame to a patient's head such that locations within the head are spatially definable with reference to frame. The fixation structure includes a cast of the patient's upper teeth and/or palate. The fixation structure further includes a support for rigidly connecting the cast to the frame and biasing structure operable between the head and the frame and/or the fixation structure to bias the cast into positive contact with the upper teeth and/or palate. The apparatus is used in stereotatic diagnosis and treatment.

10 Claims, 13 Drawing Sheets

U.S. PATENT DOCUMENTS

Figure 1:
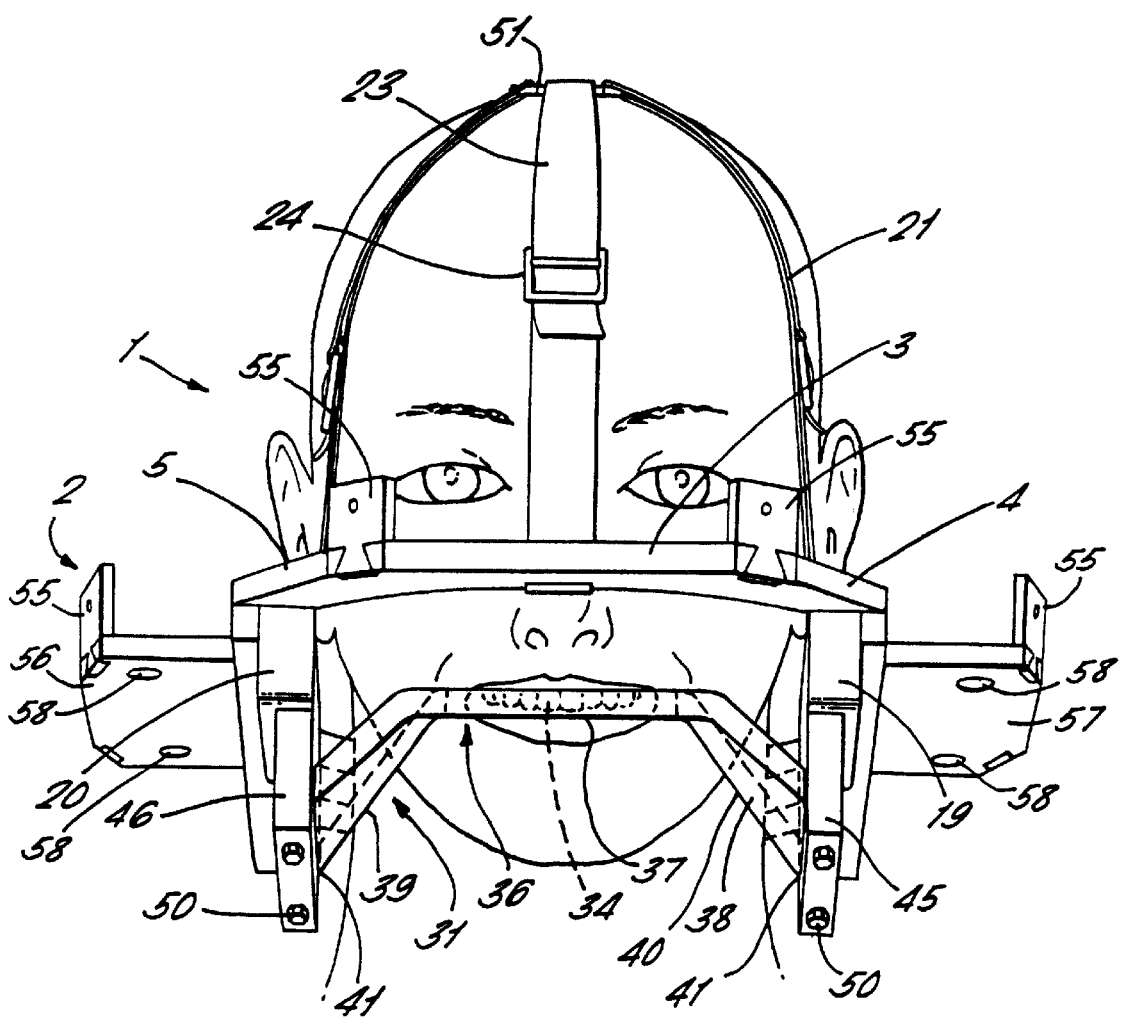

| | | | |
|---|---|---|---|
| 3,983,474 A | | 9/1976 | Kuipers |
| 4,182,312 A | | 1/1980 | Mushabac |
| 4,228,799 A | * | 10/1980 | Anichkov et al. ........... 606/130 |
| 4,256,112 A | * | 3/1981 | Kopf et al. ................. 606/130 |
| 4,262,306 A | | 4/1981 | Renner |
| 4,319,136 A | | 3/1982 | Jinkins |
| 4,341,220 A | | 7/1982 | Perry |
| 4,358,856 A | | 11/1982 | Stivender et al. |
| 4,386,602 A | | 6/1983 | Sheldon et al. |
| 4,398,707 A | | 8/1983 | Cloward |
| 4,463,758 A | | 8/1984 | Patil et al. |
| 4,465,069 A | | 8/1984 | Barbier et al. |
| 4,506,676 A | | 3/1985 | Duska |
| 4,583,538 A | | 4/1986 | Onik et al. |
| 4,592,352 A | | 6/1986 | Patil |
| 4,598,368 A | | 7/1986 | Umemura |
| 4,602,622 A | | 7/1986 | Bar et al. |
| 4,608,977 A | | 9/1986 | Brown |
| 4,617,925 A | | 10/1986 | Laitinen |
| 4,618,978 A | | 10/1986 | Cosman |
| 4,638,798 A | | 1/1987 | Shelden et al. |
| 4,645,343 A | | 2/1987 | Stockdale et al. |
| 4,694,478 A | * | 9/1987 | Delnon ....................... 378/170 |
| 4,701,049 A | | 10/1987 | Beckmann et al. |
| 4,705,395 A | | 11/1987 | Hageniers |
| 4,705,401 A | | 11/1987 | Addleman et al. |
| 4,706,665 A | | 11/1987 | Gouda |
| 4,709,156 A | | 11/1987 | Murphy et al. |
| 4,722,056 A | | 1/1988 | Roberts et al. |
| 4,722,336 A | | 2/1988 | Kim et al. |
| 4,733,661 A | | 3/1988 | Palestrant |
| 4,750,487 A | | 6/1988 | Zanetti |
| 4,791,934 A | | 12/1988 | Brunnett |
| 4,797,736 A | | 1/1989 | Kloots et al. |
| 4,805,615 A | | 2/1989 | Carol |
| 4,836,778 A | | 6/1989 | Baumrind et al. |
| 4,838,265 A | | 6/1989 | Cosman et al. |
| 4,845,626 A | | 7/1989 | Ohhashi |
| 4,859,181 A | | 8/1989 | Neumeyer |
| 4,869,247 A | | 9/1989 | Howard, III et al. |
| 4,875,478 A | | 10/1989 | Chen |
| 4,884,566 A | | 12/1989 | Mountz et al. |
| 4,945,914 A | | 8/1990 | Allen |
| 4,955,891 A | | 9/1990 | Carol |
| 4,985,019 A | | 1/1991 | Michelson |
| 4,991,579 A | | 2/1991 | Allen |
| 5,027,818 A | | 7/1991 | Bova et al. |
| 5,078,140 A | | 1/1992 | Kwoh |
| 5,116,344 A | | 5/1992 | Sundqvist |
| 5,142,930 A | | 9/1992 | Allen et al. |
| 5,154,179 A | | 10/1992 | Ratner |
| 5,165,410 A | | 11/1992 | Warne et al. |
| 5,178,146 A | | 1/1993 | Giese |
| 5,186,174 A | | 2/1993 | Schlondorff et al. |
| 5,230,338 A | | 7/1993 | Allen et al. |
| 5,247,555 A | | 9/1993 | Moore et al. |
| 5,251,127 A | | 10/1993 | Raab |
| 5,305,203 A | | 4/1994 | Raab |

FOREIGN PATENT DOCUMENTS

| | | |
|---|---|---|
| EP | 0 326 768 | 8/1989 |
| FR | 1282623 | 12/1961 |
| FR | 2417-970 | 10/1979 |
| GB | 2 094 590 | 9/1982 |
| JP | 62-327 | 6/1987 |
| SU | 0766581 | 9/1980 |
| SU | 0955916 | 9/1982 |
| WO | WO88/09151 | 12/1988 |

OTHER PUBLICATIONS

Greitz, T., "Head Fixation System for Integration of Radiodiagnostic and Therapeutic Procedures", *Neuroradiology*, vol. 19, pp. 1–6, (1980).

Jacques, Skip et al., "A Computerized Microstereotactic Method to Approach, 3–Dimensionally Reconstruct, Remoe and Adjuvantly Treat Small CNS Lesions", Appl. Neurophysiol. 43:176–182 (1980).

Kosugi, Yukio et al., "An Articulated Neurosurgical Navigation System Using MRI and CT Images", *IEEE Transactions on Biomedical Engineering* vol. 35, No. 2, pp. 147–152 Feb. 1988 (article).

Lavallee, S. et al., "Computer Assisted Puncture", Reconnaissance Des Formes et Intelligence Artificielle, 6th Congres Exposition, vol. 1, 439–49, Nov. 16–20, 1987.

Pelizzarik C.A. et al., "Interactive 3D Patient—Image Registration", (date unknown).

Reinhardt, H. et al., "A Computer–Assisted Device for the Intraoperative CT–Correlated Localization of Brain Tumors", *Eur. Surg. Res.*, pp. 51–58, No. 20, 1988.

Roberts, David W. et al., "Frameless Stereotaxic Integration of Computerized Tomography Imaging and The Operating Microscope", J. Neurosurg. 65:545–549 (1986).

Watanabe Eiju et al."Three–Dimensional Digitizer (Neuronavigator): New Equipment for Computed Tomography–Guided Stereotaxic Surgery", *Surg. Neurol.* pp. 543–547, No. 27, 1987.

Watanabe, Hideyasu, "Neuronavigator", Igaku–no–Ayumi (Medical Progress), vol. 137, No. 6 (May 10, 1986).

Westover, Joseph L. et al., Transnasal Hypophysectomy: Technic and Dosimetry, *Radiology*, vol. 74, No. 1, pp. 86–87 (Jan. 1960).

2 copies of photographs showing the Rand–Wells stereotaxic device of the Greitz et al. article in greater detail.

* cited by examiner

HEAD FIXATION APPARATUS

This is a continuation of Ser. No. 08/872,456 filed Jun. 10, 1997, now abandoned which is a continuation of Ser. No. 08/639,324 filed Apr. 25, 1996, now abandoned which is a continuation of Ser. No. 08/472,731 filed Jun. 7, 1995, now abandoned, and a continuation of Ser. No. 08/283,921 filed Aug. 1, 1994, now abandoned, which is a continuation of Ser. No. 08/023,480 filed Feb. 25, 1993, now abandoned which is a continuation of Ser. No. 07/911,351 filed Jul. 8, 1992, now abandoned which is a continuation of Ser. No. 07/787,764 filed Nov. 6, 1991, now abandoned which is a continuation of Ser. No. 07/673,858 filed Mar. 21, 1991, now abandoned which is a continuation of Ser. No. 07/568,524 filed Aug. 14, 1990, now abandoned which is a continuation of Ser. No. 07/278,270 filed Oct. 30, 1988, now abandoned.

This invention relates to head fixation apparatus primarily but not exclusively for use in stereotactic procedures for diagnosis and treatment of the brain.

A number of different imaging techniques are available for diagnosis and monitoring of neurological conditions including computerised tomography, positron emmision tomography, magnetic resonance imaging, magnetic resonance spectroscopy, and digital subtraction angiography. It is often desirable that imaging be carried out periodically and for images from different types of apparatus to be integrated or correlated. A problem in each case arises in repeatably positioning the patient's head in a precise location relative to each imaging apparatus and defining a co-ordinate system enabling different apparatus to be used to image the same image plane.

A number of stereotactic surgical techniques are based on imaged information and it is also a common requirement for stereotactic procedures such as biopsies to be carried out at the same location within a patient's head on a number of separate occasions over a long term period of treatment. Examples of such surgical procedures would be the biopsy of a tumour and the draining of cysts.

It is known to provide head fixation apparatus comprising frame means attachable to stereotactic surgical and or imaging apparatus and fixation means for fixing the frame means onto a patient's head in a substantially reproducible manner such that the location of anatomical features and their corresponding images can be spatially defined with reference to the frame means.

The co-ordination of stereotactic imaging and surgical procedures has for example been achieved by means of head fixation apparatus in which a frame means is a rigid metal frame fixed to a patient's head so that a three dimensional coordinate system can be defined with reference to the frame. Biomedical images can then be characterised with reference to this coordinate system and the co-ordinates used as control parameters for stereotactic procedures. A guide for a surgical probe can for example be attached to the frame and used to guide the probe to co-ordinates within the brain which have been calculated from an image that may have been produced sometime earlier at a different location having the appropriate imaging facilities.

For satisfactory correlation to be achieved it is necessary that the fixation means by which the frame means is fixed to the patient's head provides precise and repeatable location of the frame means with reference to the patient's fixed anatomical features i.e. the skull bones.

It is known for the fixation means to comprise rods or screws which penetrate holes in the patient's skull and which support a frame means in the form of a base ring. Imaging apparatus or stereotactic surgical instruments may then be connected to the base ring. A number of disadvantages are associated with this fixation means, primarily because of its invasive nature which requires sterility and anaesthesia and results in patient trauma. The reproducibility available with this technique is also limited because the bore holes become obstructed by debris and will heal over in time preventing long term relocations.

A number of non-invasive techniques have been proposed of which GB-2164856 (Laitinen) discloses fixation means for a reference frame comprising two ear plugs and a naison support. A disadvantage of this apparatus is that the ear plugs and naison support each contact relatively soft tissue so that to minimise movement of the frame means a degree of force needs to be applied to the ear plugs and naison support which is uncomfortable for the patient and prevents the apparatus being tolerated for more than about 20 minutes. This factor makes the apparatus unsuitable for the prolonged studies demanded in some imaging techniques such as positron emmission tomography. A further disadvantage is that the particular apparatus disclosed is insufficiently robust to serve as a secure base for surgical instruments.

It is also known to mould a helmet conforming to the shape of the top part of a patient's head using either thermosetting material or fibreglass/resin techniques and to inset metallic supports into the helmet upon which to mount a frame. Such systems are described by T. Greitz et al in Neuroradiology 19, 1–6(1980).

This publication discloses the use of a dental mould in conjuction with a fibreglass bandage to provide a mouth piece receiving an impression of the patient's upper incisor teeth.

A disadvantage of such skull cap techniques is their inherent lack of reproducibility due to the presence of soft tissue between the cap and the skull. The skin in this area is also not firmly fixed to the skull and tends to allow movement of the cap. In the case of a skull cap in which a mouth piece is provided having an impression of the upper incisors it is found that cap movement tends to be pivotal about the incisors. Consequently this technique has not been found to be practicable in general use.

It is also known to provide fixation apparatus where reference is made to the patient's teeth as in the case of the Rand-Wells stereotactic device referred to in Radiology Volume 74 No. 1 pages 86 to 87 January 1960. Although not disclosed in this publication the Rand-Wells device in use includes a mouthpiece having a U-shaped tray into which dental cast material is received to make a cast of the patient's upper teeth. Subsequent to alignment with the teeth three pointed screws are fastened to the skull through the skin such that a framework is rigidly and precisely fixed to the head. The Rand-Wells device has been used for procedures in which radio active seeds are implanted into the pituitary gland through the nasal cavities. The invasive nature of the screws leads to the disadvantages of other invasive techniques discussed above.

According to the present invention there is disclosed apparatus for use in stereotactic diagnosis and treatment comprising frame means, or frame assembly, and fixation means, or fixation member, for repeatably and reproducibly fixing the frame means to the patient's head such that locations within the head are spatially definable with reference to the frame means, wherein the fixation means comprises a cast of the patient's upper teeth and or palate, the fixation means further comprising support means for rigidly connecting the cast to the frame means and biasing means non-invasively engageable with the head and operable between the head and the frame means and or the fixation means to bias the cast into positive contact with the upper teeth and or palate.

Preferably the fixation means comprises a cast comprising a U-shaped portion indented with an impression of substantially all of the patient's upper teeth if any.

An advantage of such an arrangement is that the teeth provide the most rigid point of non-invasive location on the skull and are able to withstand comfortably considerable firm pressure particularly when distributed over the complete set of teeth.

Advantageously the cast has a contact surface which in use engages in intimate contact the inner and inferior aspects of all of the patient's upper teeth.

It is thereby possible to make the cast conform to the numerous contours provided by the patient's teeth so that the cast locates in a unique position. This also avoids the problem of the undercut provided by the incisor teeth in that a cast which also fitted intimately over the entire inner and outer surface of these incisor teeth would not be removable without splitting the cast.

Preferably the contact surface further engages the outer aspect of the molar and premolar teeth.

Additional locating points are thereby established without preventing the cast from being removed since these teeth in general do not include an undercut.

The cast may include also a bridge portion conforming to the palate and forming a continuous bridge between the arms of the U-shaped portion.

The hard palate is also capable of comfortably taking high loads when evenly distributed and of giving reliable relocation characteristics because it is formed by a thin layer of a membrane (mucoperiosteum) which is firmly fixed to the underlying palate bone. This membrane is approximately one millimetre in thickness and is not only relatively incompressible compared with other skin areas but also does not tend to slide on the bone unlike skin covering the scalp.

The palate is dome like in shape and is therefore well suited for restraining the cast against movement in all directions other than downward.

The upper palate bone is also ridged and the membrane conforms to this ridging thereby providing additional means for positively locating the cast.

Such a bridge arrangement has the advantage of providing considerable strength to the cast since a bridge or dome like configuration has improved dimensional stability under compressive loading.

The bridge portion may be omitted where the patient's upper teeth are such as to provide adequate seating of the cast in that, when biassed into contact with the teeth the cast is firmly located in a stable fixed position. The omission of the bridge under these conditions facilitates speech by the patient which would otherwise be impaired by restricted tongue movement.

Preferably the support means comprises a plate having a central portion connected to the front of the cast so as to be generally coplanar with the U-shaped portion and side portions which extend rearwardly inside of the patient's mouth in supporting contact with the cast to at least as far as the location of the premolar teeth.

Preferably the plate includes side portions which extend rearwardly outside of the patient's mouth to at least as far as the location of the premolar teeth.

Such an arrangement allows a load to be applied to the cast in a direction which is upwards with respect to the normal orientation of the skull with the load being directed in the region of the premolar teeth. This configuration has been found to be most comfortable and stable in use.

Advantageously the side portions extend at a downwardly inclined angle with respect to the central portion.

The plate is thereby formed in an arch configuration which is dimensionally stable under load.

The support means may include a tray connected to the plate and containing a layer of a material which is initially indentable so as to take an impression of the patient's upper teeth and/or palate and which is subsequently cured to a rigid form retaining the impression formed therein.

Conveniently the apparatus includes demountable connecting means operable between the fixation means and the frame means.

It is then possible to use the same frame means with a plurality of different fixation means adapted to corresponding individual patients by including casts of their own teeth and or palate.

Conveniently such connecting means are provided by vertical location plates connected to the side portions of the support means and having screw fittings operable between the location plates and the frame means.

Advantageously the side portions are fixed to the location plates after an initial positioning procedure during which the frame means is supported at a desired position and the corresponding relative positions of the side portions and the location plates are recorded. The side portions may be fixed to the location plates by screw fittings or by adhesive bonding.

Such an arrangement enables the frame means to be positioned relative to the patient's head in a manner which is adapted to the patient's individual physical dimensions and the position and nature of the abnormality requiring investigation and treatment. The frame means can thereby be used on any number of different patients without modification and those parts of the apparatus which are specific to a particular patient are contained in a single unit which can be conveniently stored.

Preferably the apparatus includes positioning arc means detachably connectable with the frame means and defining a working space relative to the frame means which is equal to or less than the corresponding working space required by stereotactic instruments or the like which are to be subsequently fitted to the frame means in use whereby the initial positioning procedure carried out with the arc so connected ensures the frame means is positioned relative to the head so as to maintain working clearance between the head and any such instrument.

Such an arrangement avoids the need to carry out the initial positioning procedure whilst the patient's head is positioned within the stereotactic instrument to be used. The arc means may also be formed from a lightweight material which enables the apparatus to be easily manoeuvred during the initial positioning procedure.

Conveniently the biassing means comprises straps connected to the frame means and extending over the top of the patient's head.

Preferably the biassing means further includes a headrest connected to the frame means and engageable with the lower rear portion of the head to resist forward tilting on the frame means.

The biassing means may then operate by tightening the straps so that the frame means is biassed upwardly with a thrust directed generally at its centre. Since the cast is located at the front of the skull there is a tendency for forward tilting to arise since the downward reaction on the frame means from the patient's teeth and palate is located at the front of the frame. By including the headrest a downward reaction at the rear of the frame means is provided which enables the frame means to be stable under loaded conditions.

Advantageously the headrest includes a cushion comprising a flexible casing containing a granular material and having means for evacuating air from the casing. Such a cushion can be intimately moulded to the shape of the head and becomes a ridged support once the air has been evacuated from the casing. Alternatively the cushion may be inflatable with air or liquid to assist distribution of loading on the head.

Preferably the apparatus includes ear supports comprising ear plugs detachably connectable by adjustable supports to the frame means. Such ear plugs are useful in fitting the apparatus and assist in maintaining the correct alignment of the frame means prior to tightening of the staps and positioning of the headrest.

Alternatively the headrest may comprise a rigid pad moulded to the occipital region of the patient's head and calibrated adjustment means operable between the pad and the frame means for repeatably positioning the pad at co-ordinates specific to each patient. The use of ear plugs referred to above would in this arrangement then be unnecessary.

Conveniently the frame means comprises a U-shaped frame member and a U-shaped bracket upon which the headrest is mounted and being connectable with the frame member to form a closed annular frame and adjustment means facilitating adjustment of the relative positions of the frame member and bracket to thereby adjust the position of the headrest relative to the head.

Preferably the frame means and fixation means comprise non metallic and insulating materials.

Such materials do not introduce artefacts under most imaging systems including magnetic resonance imaging.

Such apparatus may nevertheless include fiducial features which are specifically selected from visible materials under the required imaging system for example where it is required to calibrate a system prior to or during use.

Preferably the apparatus further comprises a frame holder detachably connectable to the frame means and having means for connection to biomedical scanning apparatus and having means for adjusting the position of the frame means relative to the frame holder in a plane which is parallel with the plane imaged by the scanning apparatus.

Such an arrangement ensures that all scanned images obtained using such scanning apparatus are taken in parallel planes. In conventional scanning apparatus a series of images are taken at planes which are parallel to each other and spaced apart by regular intervals and it is important that no tilting of the patient's head occurs between the taking of subsequent images.

A particular advantage of the present invention when used in this way is that the frame holder may be attached to a number of different types of biomedical scanning apparatus thereby allowing subsequent scans using different apparatus to be taken at the same plane relative the patient's head. Furthermore by taking a series of scans which are spaced apart by the same distance for each apparatus it is possible to integrate the biomedical images obtained by different scanning apparatus using appropriate computer techniques.

This is particularly useful for example when using positron emission tomography which does not produce images of the patient's skull. It is possible in accordance with the present invention to correlate and integrate such images with computerised tomography scans which image the patient's skull so that after subsequent processing the features imaged on the positron emission tomography scan can be visually related to the skull.

A further advantage of the use of such a frame holder is to enable the patient's head to be repeatably positioned within apparatus for irradiating a localised area within the skull.

Figure 2:
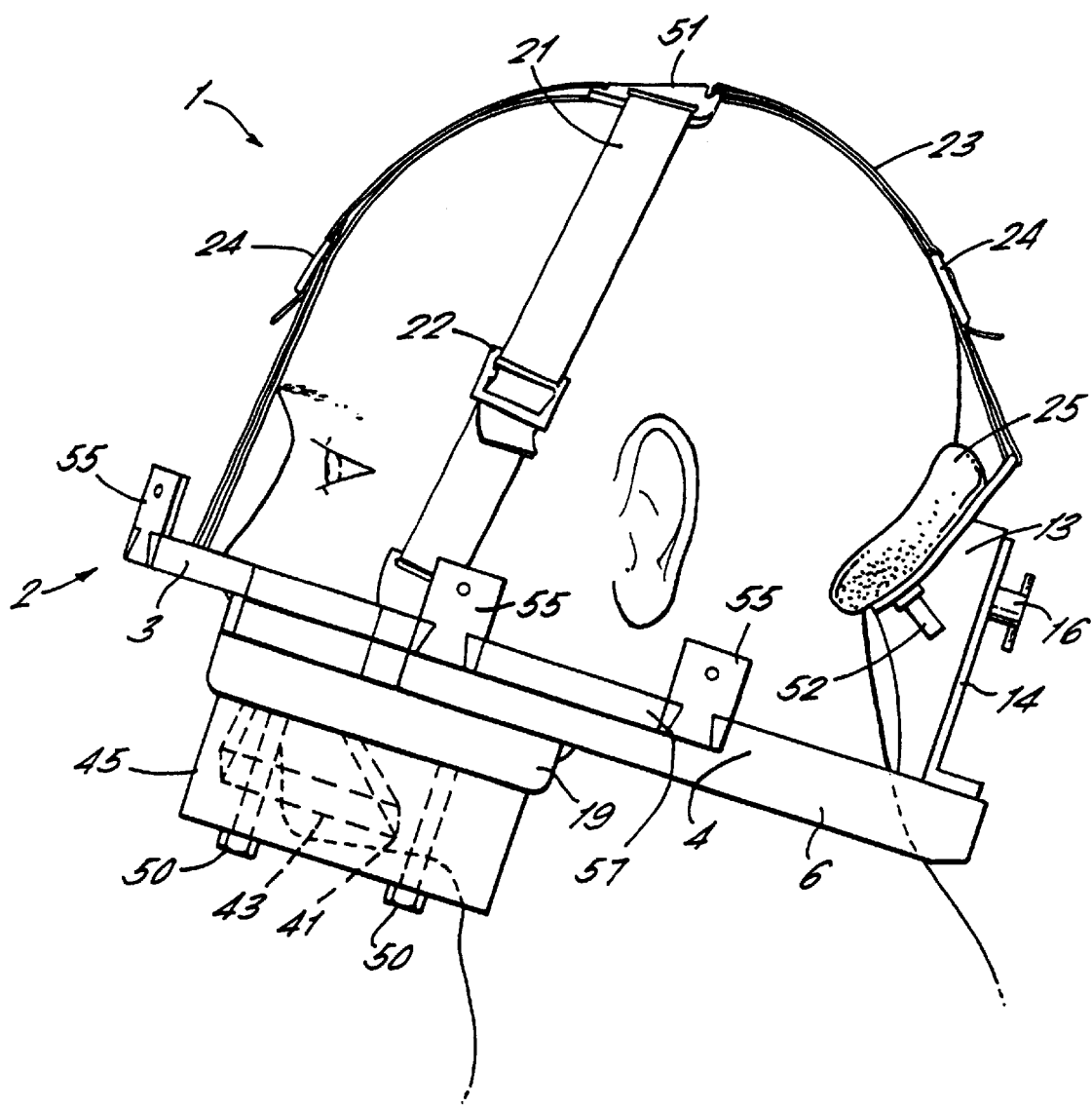
Figure 3:
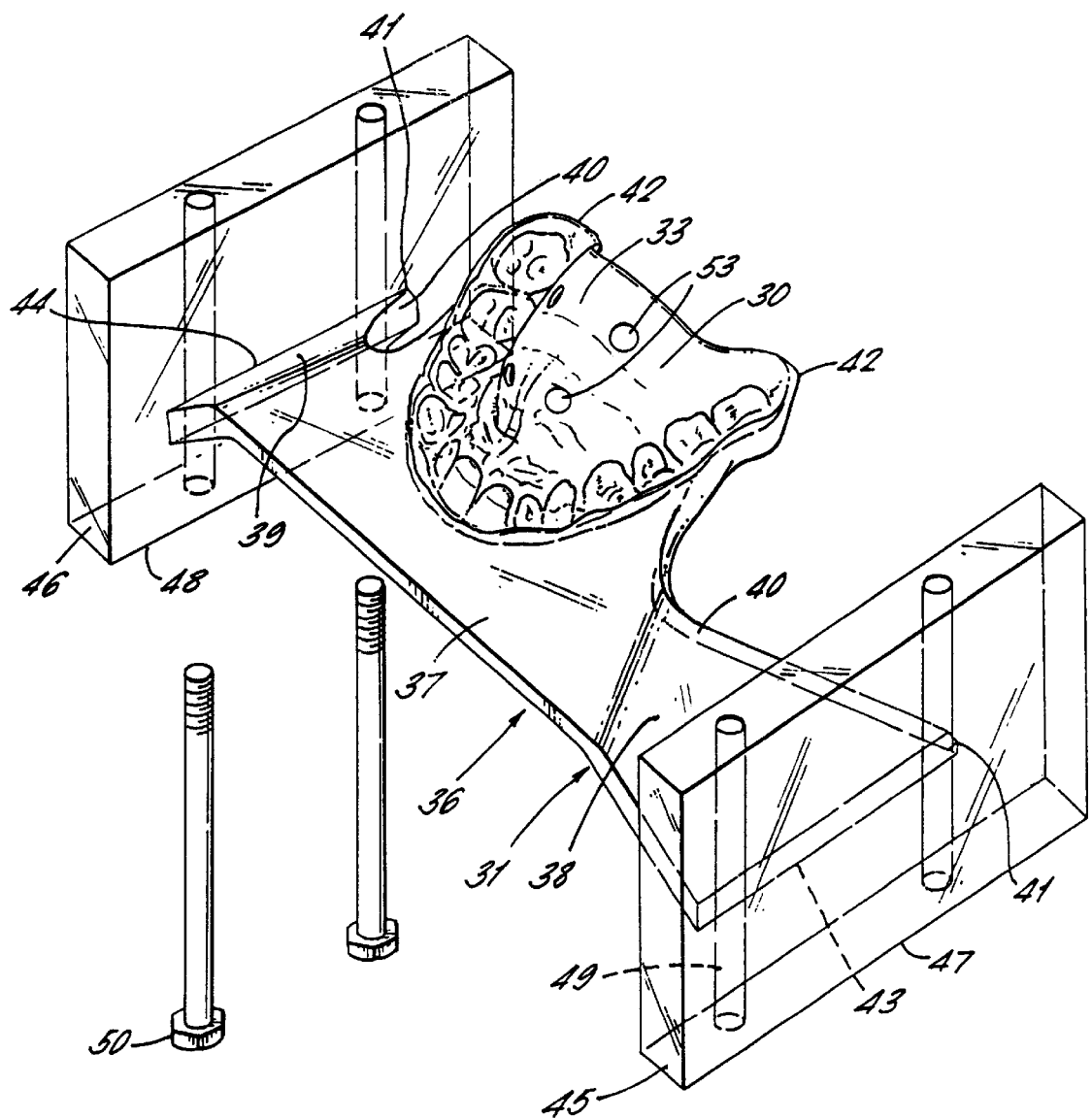
Figure 4:
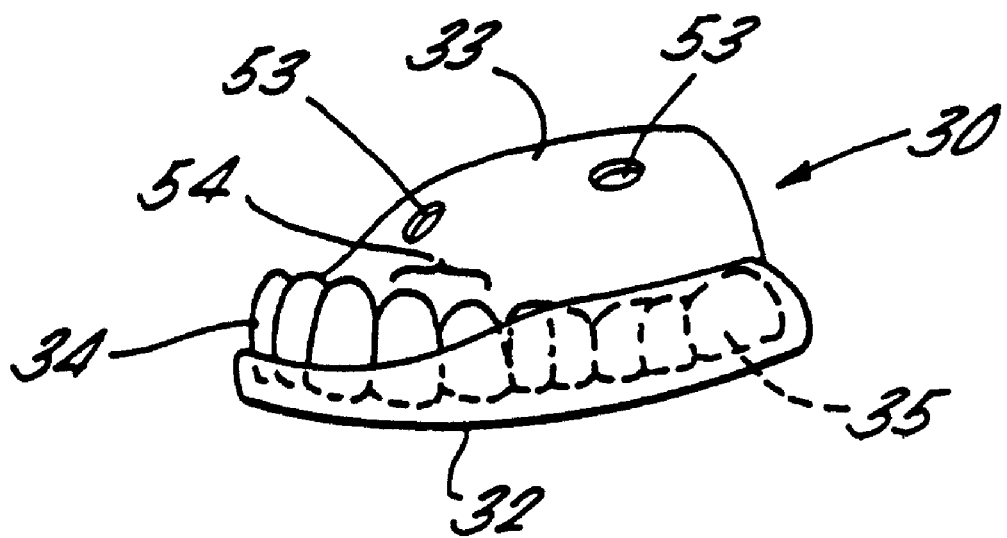
Figure 5:
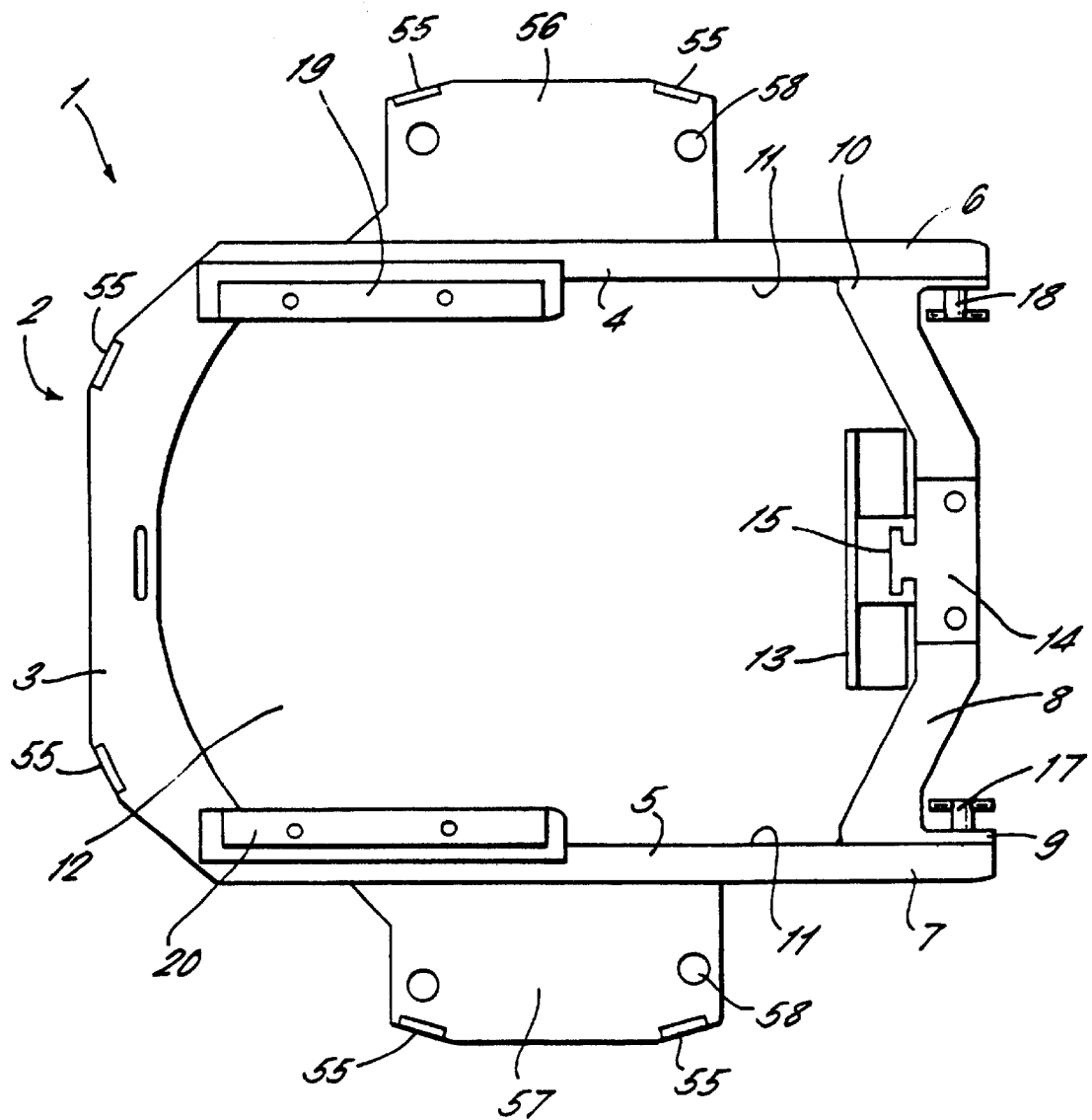
Figure 6:
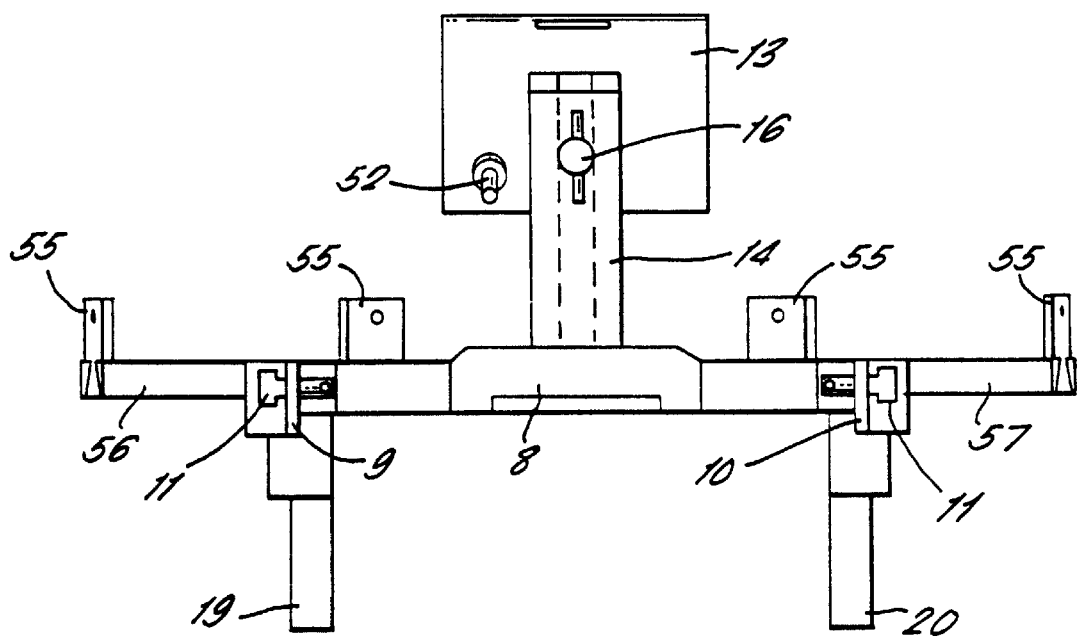
Figure 7:
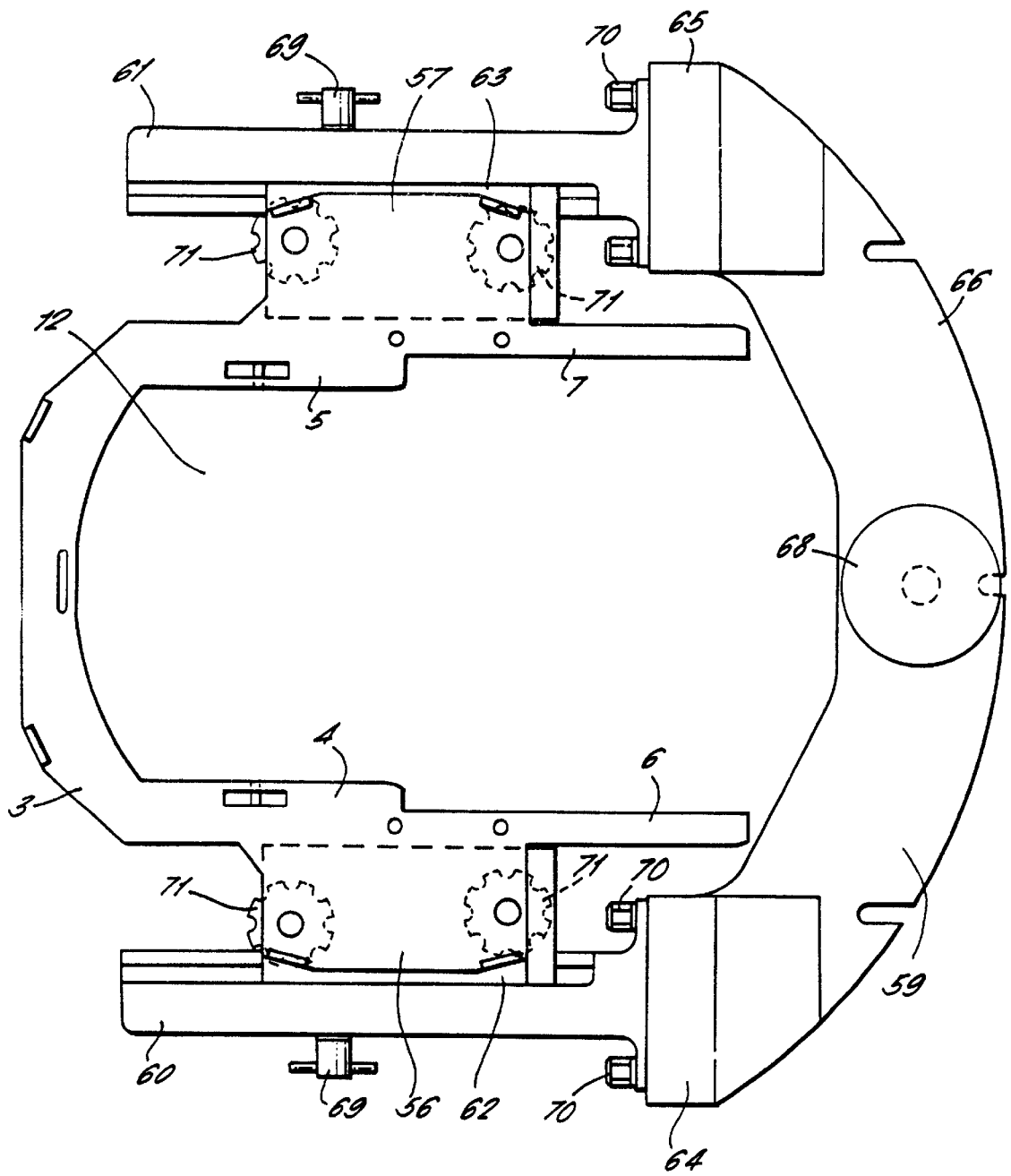
Figure 8:
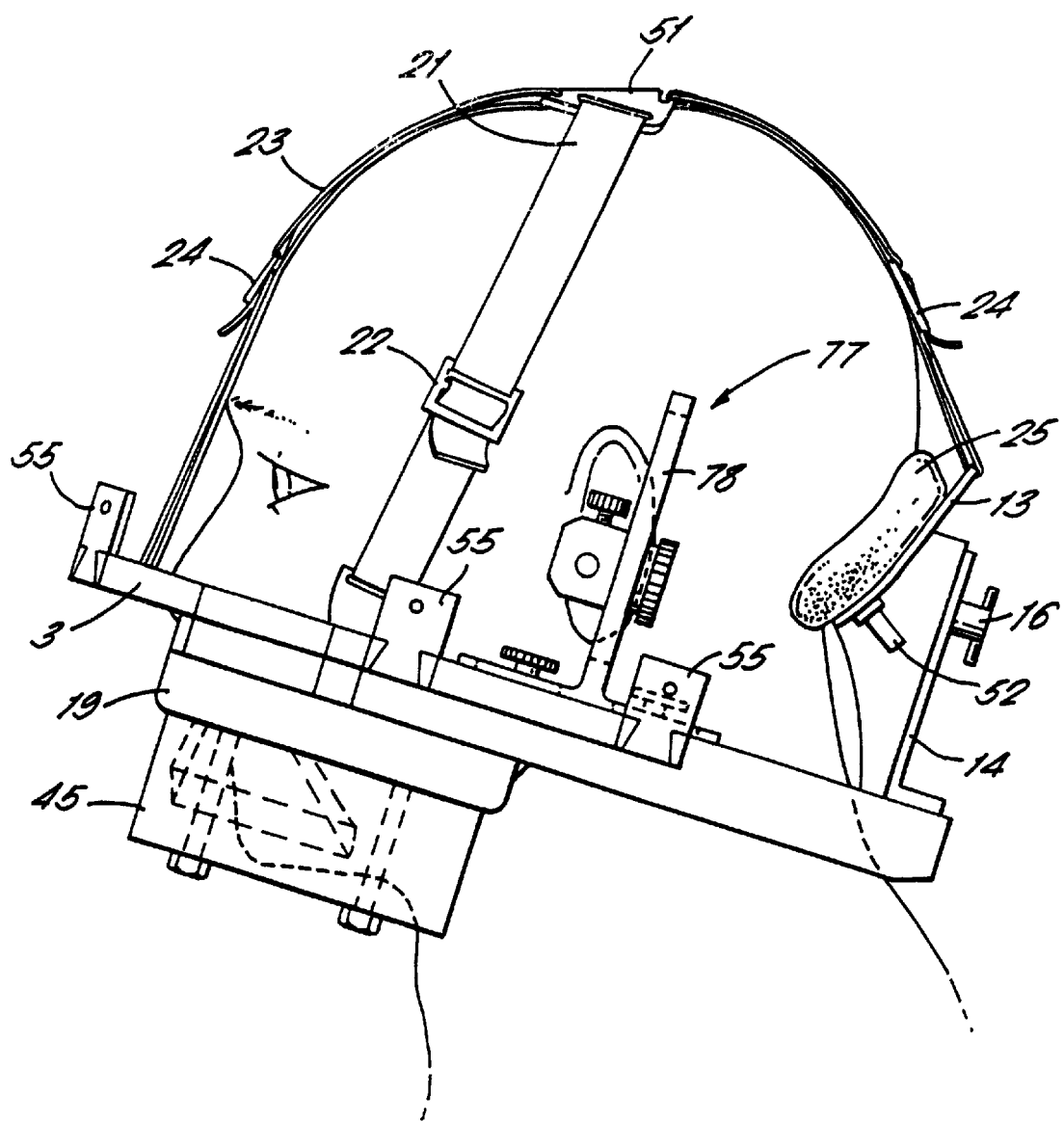
Figure 9:
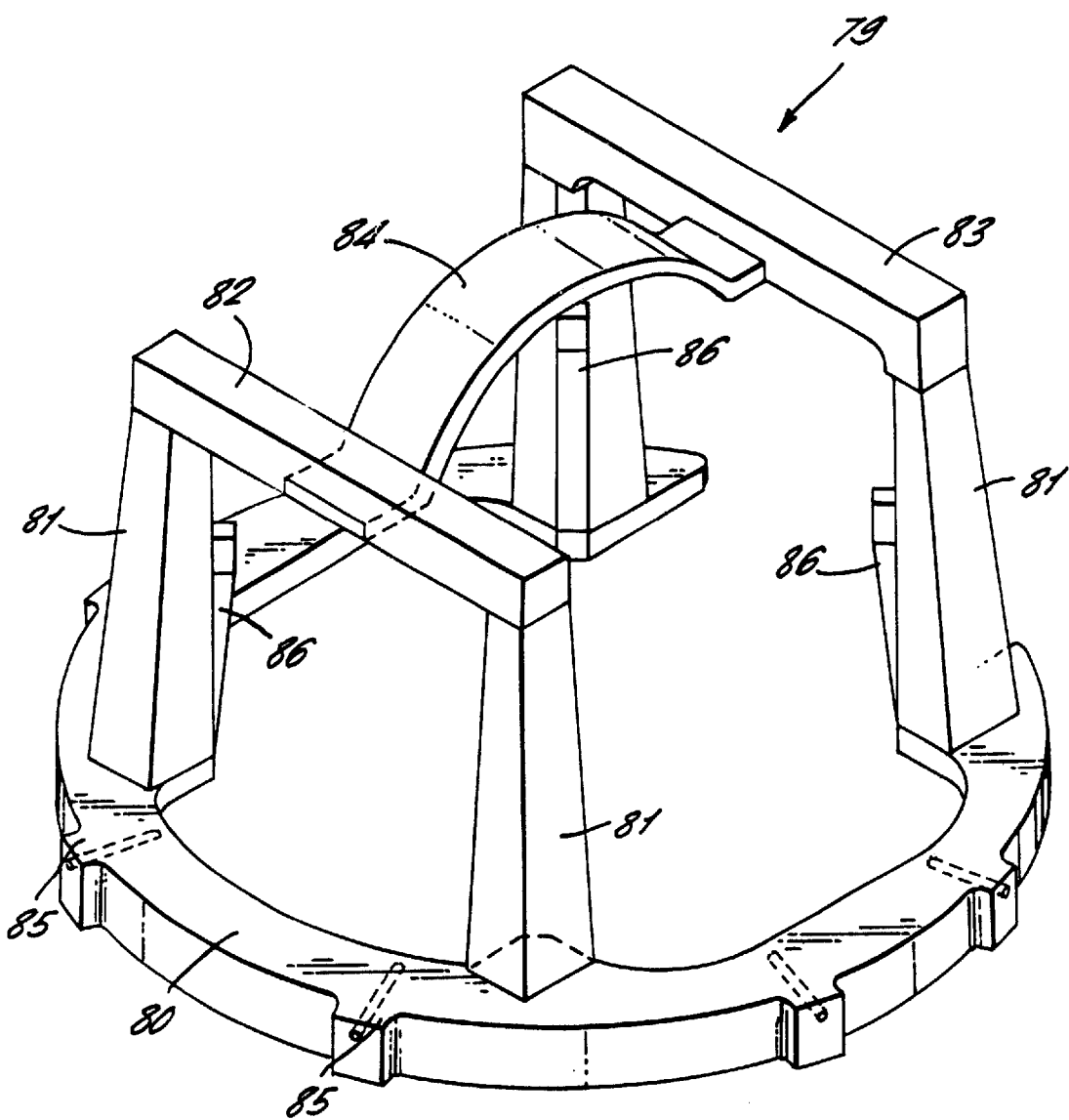
Figure 10:
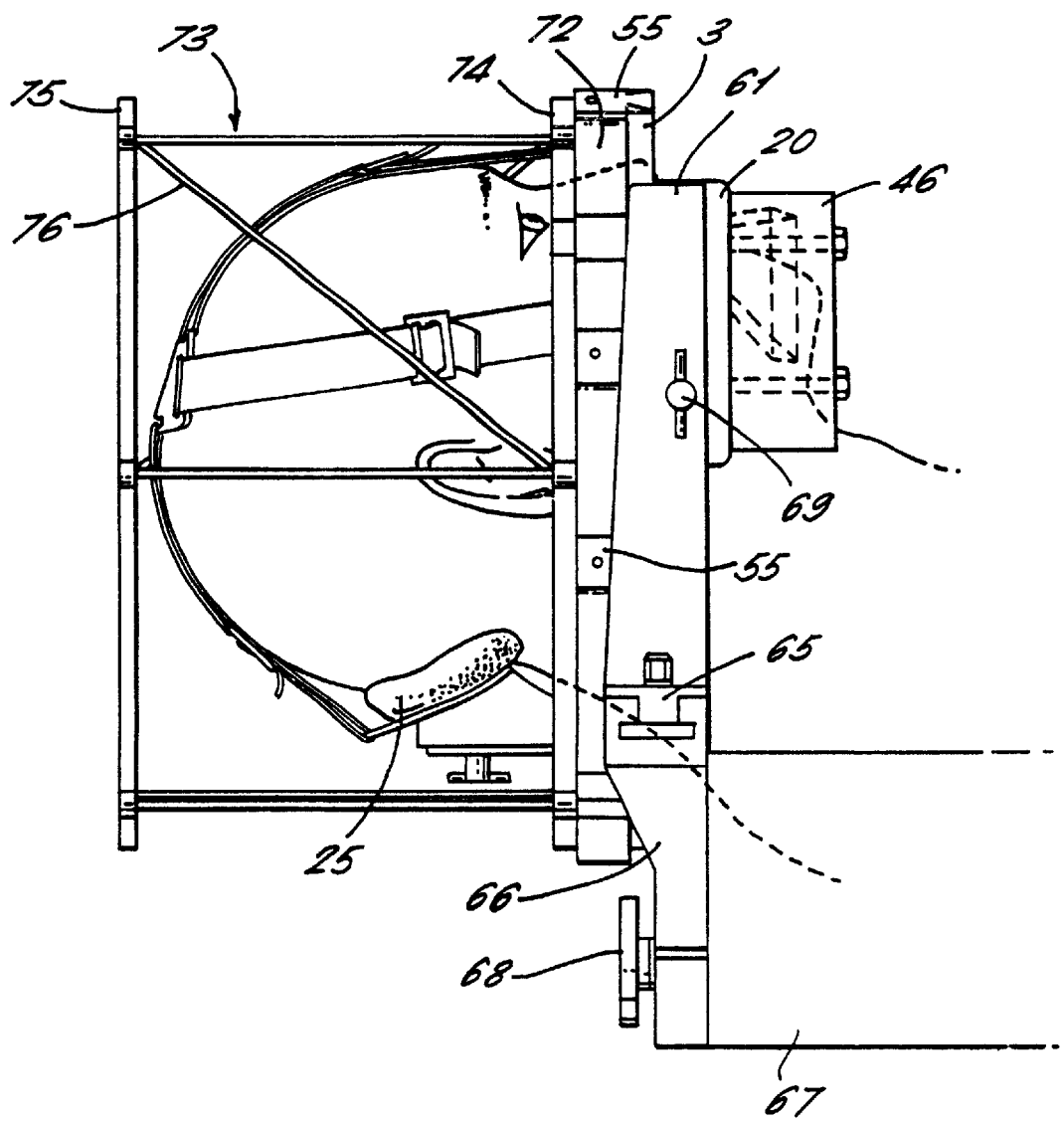
Figure 11:
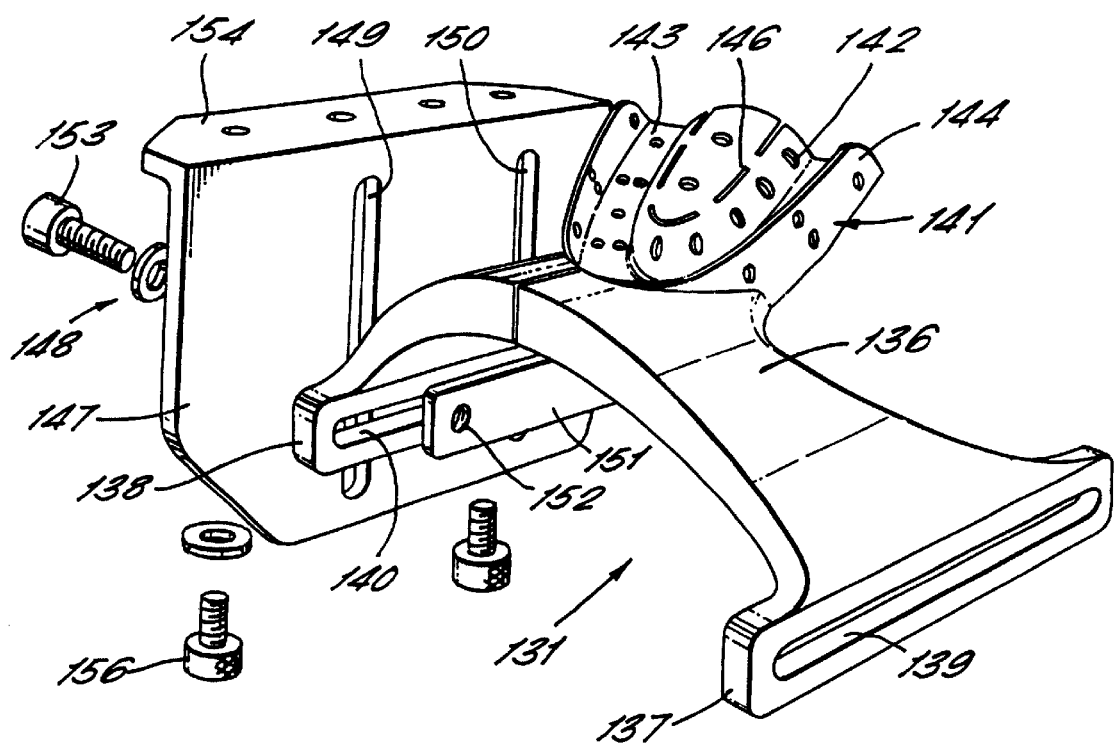
Figure 12:
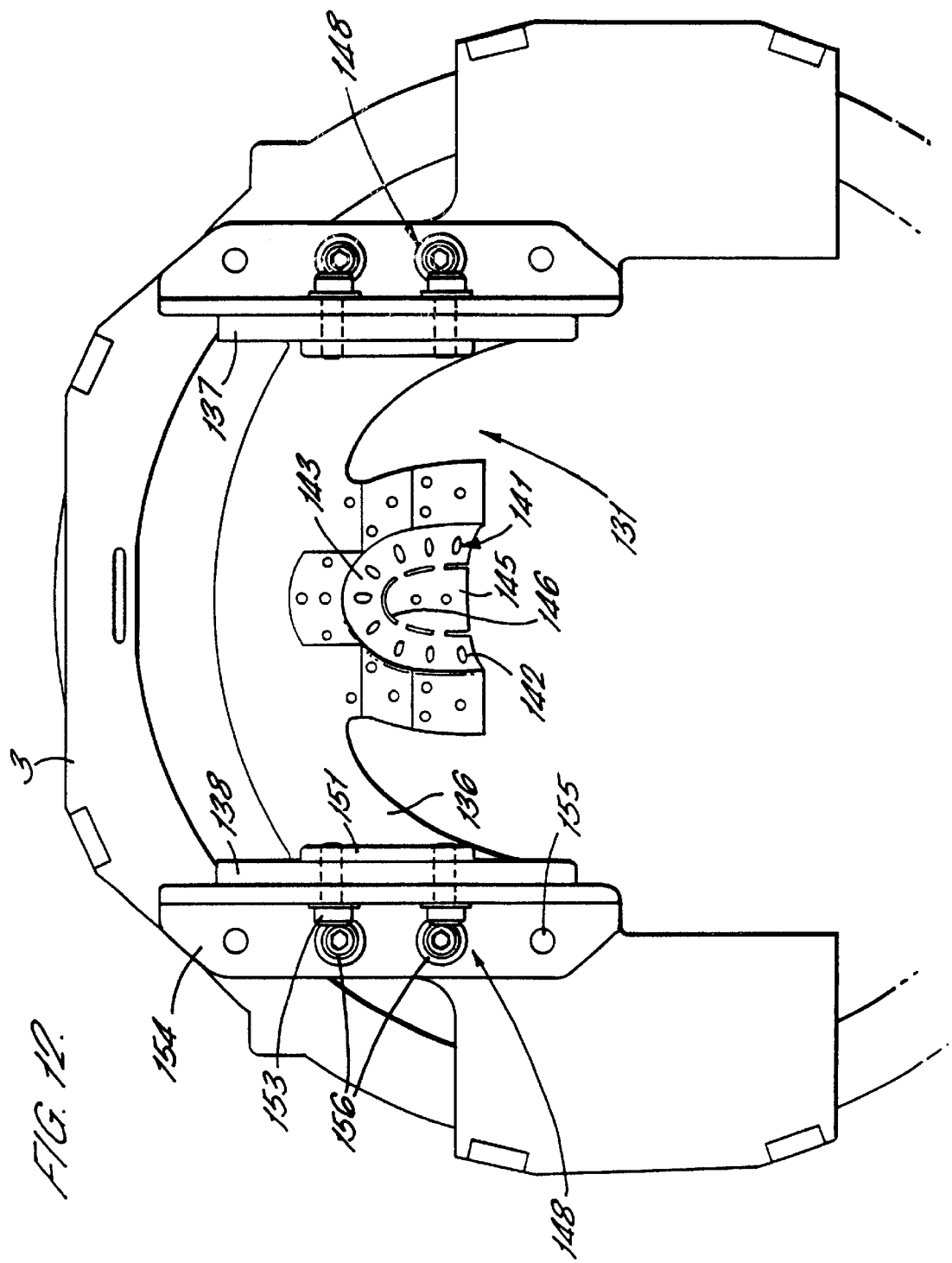
Figure 13:
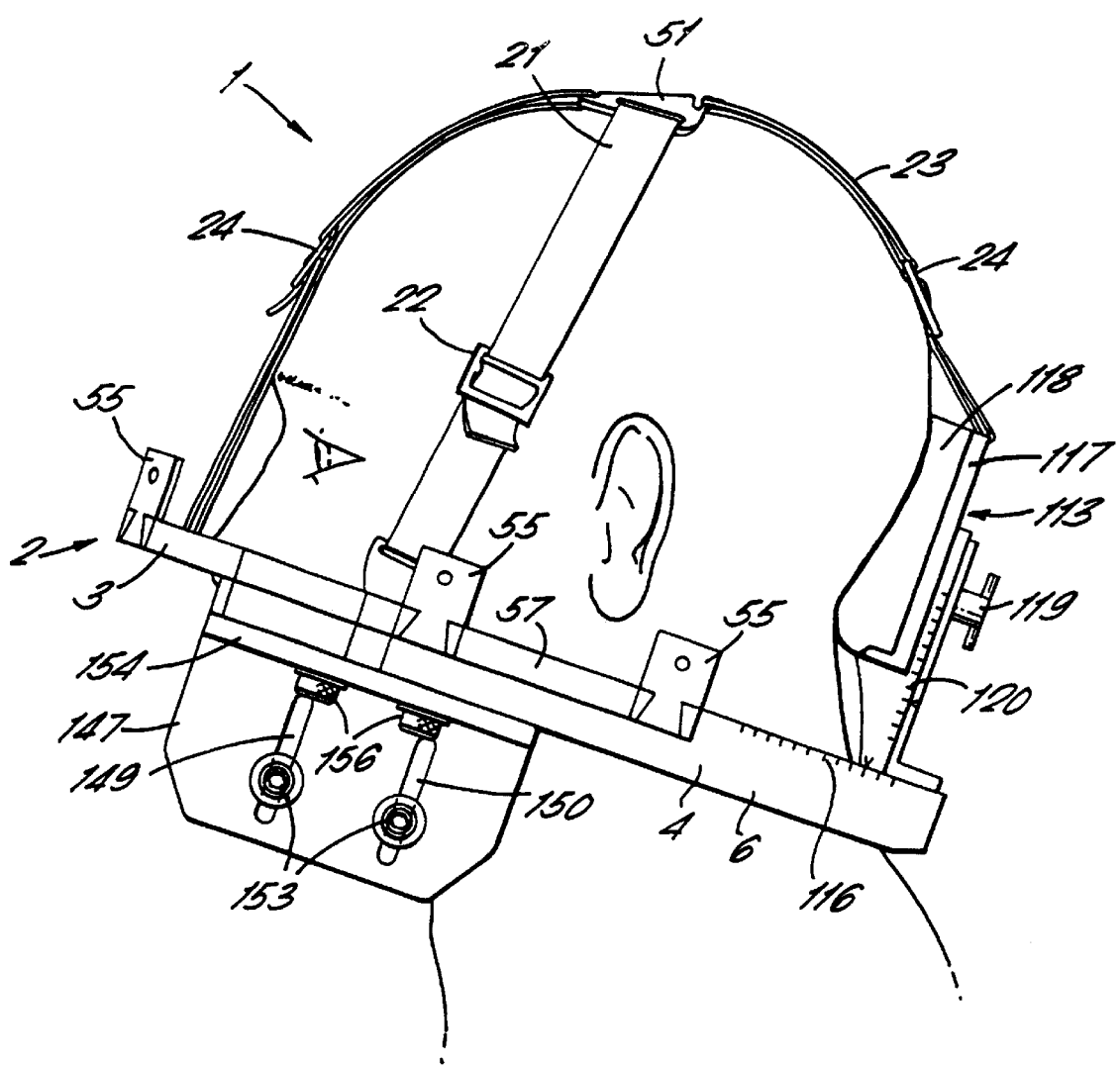

A particular embodiment of the present invention will now be described by way of example only and with reference to the following drawings of which:

FIG. 1 is a front view of apparatus in accordance with the present invention and fixed to a patient's head, FIG. 2 is a side view of the arrangement shown in FIG. 1, FIG. 3 is a perspective view of a cast and support means of the apparatus of FIGS. 1 and 2, FIG. 4 is a perspective view of the cast of FIG. 3 and showing the relative position of the patient's upper teeth, FIG. 5 is an underneath view of the frame means of the apparatus of FIGS. 1 and 2, FIG. 6 is a rear view of the frame means of FIG. 5, FIG. 7 is a top view of a U-shaped frame member forming part of the frame means and attached to a frame holder, FIG. 8 is a side elevation of the apparatus of FIG. 1 and including ear supports, FIG. 9 is a perspective view of a positioning arc for use in supporting the frame means during preliminary setting up procedures, FIG. 10 is a side elevation of the apparatus in use during a scan with a fiducial system connected to the frame means, FIG. 11 is a perspective view showing a support means of an alternative apparatus, FIG. 12 is an underneath view of the alternative apparatus of FIG. 11, and FIG. 13 is a side view of the alternative apparatus of FIGS. 11 and 12.

In FIG. 1 an apparatus 1 is shown fitted to a patient's head and includes a frame means 2 shown in more detail in FIGS. 5 and 6.

The frame means 2 comprises a U-shaped frame member 3 having left and right arms 4 and 5 respectively beneath which are attached guides 6 and 7 respectively which run parallel to one another on opposite sides of the patient's head.

A U-shaped bracket 8 has left and right arms 9 and 10 respectively which are slidably connected with the guides 6 and 7 by means of tongue and groove connectors 11 such that the frame member 3 and the bracket 8 together form a closed annulus defining an aperture 12 which is variable in size by relative movement of the bracket and frame member. The The bracket 8 carries a headrest 13 which is connected to the bracket 8 by an upwardly extending post 14. The headrest 13 is adjustable in height by means of a sliding connector 15 and clamp 16.

Further screw clamps 17 and 18 are provided for selectively fixing the bracket 8 in a desired position relative to the frame member 3.

The arms 4 and 5 of the frame member 3 are also connected to mounting blocks 19 and 20 which extend downwardly of the frame member on the left and right hand side of the patient respectively.

A strap 21 is connected between the left and right arms 4 and 5 and is adjustable in length by means of buckles 22. The strap 21 passes across the top of the patient's head in a lateral direction and is formed in two portions connected by a connecting element 51.

A second adjustable strap 23 is connected between the headrest 13 and the front of the frame member 3 and is adjustable in length by means of buckles 24. The second strap 23 extends over the patient's head from front to rear and is formed in two portions connected by the connecting element 51.

The headrest 13 includes a cushion 25 which in use rests against the lower rear portion (occiput) of the patient's head. The cushion 25 comprises a flexible bag containing polystyrene beads and includes a valve 52 allowing air to be evacuated from the cushion.

The apparatus 1 further includes a cast 30 and support means 31 which are seen more clearly in FIG. 3. The cast 30 is moulded in Perspex (Registered Trade Mark) with an impression of the patient's upper teeth and palate. The cast 30 comprises a U-shaped portion 32 which bears an impression of the patient's upper teeth and a bridge portion 33 which bears an impression of the patient's hard palate, the respective portions 32 and 33 being integrally formed as a single cast item.

The cast 30 includes drainage holes 53 distributed over the bridge portion 33 so as to permit drainage of saliva through the cast.

The cast 30 is individually moulded to a specific patient but in general will be in the shape of a generally planar U-shaped portion 32 with an upwardly arched bridge portion 33 extending between the opposite arms of the U-shaped portion.

As shown in FIG. 4 the U-shaped portion 32 is upturned outside of the patient's upper teeth to a lesser extent around the incisor teeth and to a greater extent around the molar teeth 35. The slight undercut exhibited by the incisor teeth 34 would otherwise inhibit the removal of the cast 30 by downward movement with respect to the teeth.

The cast 30 is formed by taking an impression of the patient's upper teeth and hard palate in a suitable plastic material, making a plaster cast of this impression and then heat shrinking a sheet of Perspex (Registered Trade Mark) over the plaster cast.

As may be seen in FIG. 3 the cast 30 is bonded by means of cold cured acrylic cement to a plate 36 having a central portion 37 and left and right side portions 38 and 39 respectively. The plate 36 is formed of Perspex (Registered Trade Mark), a thermoplastic resin of polymethyl methacylate.

The plate 36 extends laterally with respect to the patient's head, a central portion 37 being generally coplanar with the U-shaped portion 32 of the cast 30 and having a rear surface 40 which is cut away to accommodate the patient's cheeks on either side of the cast. The cut away is such as to leave sufficient plate material in supporting contact with the cast to provide support to the cast as far back as the premolar region 54 as indicated in FIG. 4. The left and right side portions 38 and 39 extend laterally of the central portion 37 and downwardly at an inclined angle relative to the horizontal of 45 degrees. Each of the side portions 38, 39 is in the shape of a truncated right angle triangle which extends rearwardly to an apex 41 located beneath the rearward extremity 42 of the cast 30.

The side portions 38, 39 terminate in straight edges 43 and 44 respectively and the plate 36 is configured such that when viewed in side projection with the central portion 37 horizontal, the edges 43 44 slope downwardly and rearwardly at and angle of 20 degrees to the horizontal.

The support means 31 further includes left and right location plates 45 and 46 respectively in the form of rectangular blocks of Perspex (Registered Trade Mark) which are bonded to the edges 43 and 44 respectively at positions determined by means of an initial positioning procedure as later described in more detail.

Vertical bores 49 extend through the location plates 45 and 46 and receive bolts 50 by means of which the support means 31 may be bolted into position beneath the frame member 3 by engaging locating holes in the mounting blocks 19 and 20.

Six lugs 55 are attached to the frame member 3 at spaced apart positions so as to extend upwardly and include locating holes for connection to various attachments described below. Left and right wing portion 56 and 57 extend horizontally on either side of the frame member 3 and include screw holes 58 for connection with attachments described below.

FIG. 7 shows one attachment in the form of a U-shaped frame holder 59 having parallel support arms 60 and 61. The frame member 3 is attached to the frame holder 59 by means of sliding blocks 62 and 63 which are slidably mounted on the support arms 60 and 61 to allow relative movement between the frame holder 59 and the frame member 3 in the forward/rearward direction, or along an axis "X" relative to the head.

The support arms 60 and 61 are mounted on bases 64 and 65 respectively which are slidably adjustable in the left/right direction, or along an axis "Y" relative to the head. The position of the frame member 3 can thereby be adjusted in both the axis "X" and the axis "Y" orthogonal directions in the plane of the frame holder 59 relative to a fixed member 66 of the frame holder. The frame holder 59 can be clamped to a table 67 of a biomedical scanner by means of a clamp 68 as shown in FIG. 10.

The frame holder 59 is provided with screw fittings 69, 70 and 71 for locking the frame member 3 in a desired position relative to the fixed member 66.

In FIG. 10 the apparatus is shown in use with a conventional head ring 72 and localiser ring assembly 73 of the BRW (Brown-Roberts-Wells) stereotactic apparatus. The head ring 72 is firmly connected to the frame member 3 by means of attachment to the lugs 55 and consists of a hardened aluminium alloy ring with mounting points for either the localiser ring assembly 73 or a stereotactic surgical instrument (not shown).

The localiser ring assembly 73 comprises a skeletal cylindrical frame in which circular end frames 74 and 75 are spaced apart by rods 76 some of which extend parallel to the cylindrical access and others being inclined thereto in order to establish a fiducial system. At least part of the rods 76 are of materials selected to be clearly imaged during the scan to establish points of reference for positional measurement.

The frame member 3 is also adapted to receive ear support attachments 77 as shown is FIG. 8 and each consisting of an ear plug and an adjustable support 78 for mounting left and right ear plugs in positions spaced above the left and right wing portions 56 and 57 of the frame member. The adjustable support 78 is for each ear adjustable in a forward/rearward direction, or along the axis "X" and in height relative to the frame member 3 aligned with an axis "Z" and also for adjustment of the depth of insertion of the ear plug.

The ear support attachments 77 facilitate stable positioning of the apparatus 1 prior to tightening of the straps 21 and 23 and adjustment of the headrest 13. The ear support attachments 77 would then be removed.

A further attachment in the form a positioning arc 79 is shown in FIG. 9 and consists of a part annular disc 80 which is shaped so as to overlay the upper surface of the frame member 3 and supports four upright members 81 at positions corresponding to the four corners of the frame member 3.

Horizontal spans 82 and 83 connect the front and rear pairs of upright members 81 and an arched strip 84 extends between the spans 82 and 83. The arched strip 84 is spaced above the disc 80 to an extent which corresponds to the maximum height of the patient's head which can be accommodated within the BRW stereotactic surgical instrument when such an instrument is connected to the frame member.

Six locating blocks 85 are provided at spaced locations around the disc 80 for connection with the lugs 55 of the frame member 3.

The upright members 81 are provided with inwardly directed projections 86 corresponding in position to posts for holding skull fixation pins (not shown) forming part of the BRW stereotactic equipment and thereby provide an indication of the preferred position of the frame member 3 relative to the patient's head when it is known that such fixation pins will subsequently be used during a surgical procedure.

In use for diagnosis and treatment of a particular patient the cast 30 must first be prepared as described above and then bonded to the plate 36. An initial positioning procedure must then be carried out before bonding the plate 36 to the left and right location plates 45 and 46.

To carry out the initial positioning procedure the positioning arc 79 is attached to the frame member 3 without the bracket 8 or the straps 21 and 23 being fitted to the frame member. The arc 79 is positioned on the patient's head after an initial investigation has revealed the general location of a pathological feature to be treated and the arc and frame are adjusted in position accordingly to ensure ease of access to the desired location.

With the location plates 45 and 46 connected to the frame member 3 the cast 30 is presented to the mouth of the patient and is adjusted in position until it fits snugly against the upper teeth and palate. The relative positions of the edges 43 and 44 of the plate 36 and the location plates 45 and 46 are recorded by for example scribing the outline of the edges 43 and 44 on the location plates. The location plates 45 and 46 are removed from the frame member and are bonded to the plate 36 at the recorded positions.

The cast 30, the plate 36 and the location plates 45 and 46 together comprise a mouth piece assembly which is uniquely identified with that particular patient. Subsequently the apparatus 1 can be used with any number of individual mouth piece assemblies for a corresponding number of patients.

Because the initial positioning procedure is carried out with the arc 79 in place the apparatus 1 can be used with BRW stereotactic equipment without danger of there being any lack of clearance between the patient's head and the equipment. The arc 79 in effect defines a working space which is equal to or less than the corresponding working space required by the BRW stereotactic equipment. When the apparatus 1 is to be used with alternative equipment then a correspondingly different positioning arc will be used which reflects the working space required by such alternative equipment.

In order to fit the apparatus 1 to the patient's head the cast 30 and support means 31 for an individual patient are assembled together with the frame member 3 by means of the bolts 50 while the bracket 8 is initially withdrawn from the frame member. The ear support attachments are fitted at this stage to the frame member 3.

The cast 30 is presented to the mouth of the patient and is adjusted in position until it fits snugly against the upper teeth and palate. The patient is asked to bite on the cast 30 to ensure positive location of the cast and the adjustable supports 78 on the ear support attachments 77 are adjusted such that the ear plugs fit into the ear canal. The ear support attachments 77 support the rear portion of the frame member 3 in the absence of any other support from straps or headrest. The bracket 8 is advanced into engagement with the frame member 3 by means of the tongue and groove connector 11 until the cushion 25 makes contact with the rear of the patient's head. The cushion 25 is moulded to the head and air evacuated to form a firm, close fitting support.

Once the headrest 13 is adjusted for comfort the clamps 16, 17 and 18 are secured.

The straps 21 and 23 are buckled over the head and are tightened by means of the buckles 22 and 24 such that the frame means 2 is biassed in the generally upward direction.

The ear plugs are then removed by releasing the adjustable supports 78 and the ear support attachments 77 are detached from the frame member 3. The function of the ear support attachment 77 is thereby completed in that the ear plugs serve to stabilise the position of the cast and frame member 3 during fitting of the straps and headrest.

With the patient sitting in a normal upright position the upper teeth are disposed in a generally horizontal plane so that the cast 30 is horizontal. The location plates 45 and 46 are in the example shown in FIG. 2 inclined at an angle of 20 degrees to the horizontal so that the frame means 2 lies generally in the plane which slopes rearwardly at an angle of 20 degrees below the horizontal. The relative positions of the frame means and the patient's head in the example shown are such that the upper surface of the frame member 3 defines a plane which is generally parallel to and spaced by approximately 4 centimetres beneath a plane passing through the eyesocket and ear canal.

The tension to which the straps 21 and 23 are tightened is such as to prevent relative movement between the cast and the patient's teeth and palate. The frame means 2 is held in a stable configuration with respect to forward or rearward tilting because it experiences an upward central force by virtue of the lateral strap 21, a forward turning moment by virtue of the reaction acting on the cast 30 and an opposing turning moment by virtue of the reaction acting on the headrest 13.

The apparatus 1 is now ready for use with either a fiducial system or a surgical instrument connected to the frame member 3. In the example shown in FIG. 10 of the BRW stereotactic system the fiducial system attached to the frame member 3 comprises the localiser ring assembly 73 which is attached to the head ring 72 mounted on the frame member. Scanner images of the patient's head will therefore include images of the fiducial system as well as those of an anatomical or pathological features and the location of those features can be defined with reference to the frame means.

Subsequent surgical procedures using the BRW system require an arc system (not shown) to be fitted to the head ring 72 in place of the localiser ring assembly 73, the arc system being such as to provide means for directing a surgical instrument to a coordinate determined during the scan.

Since the apparatus 1 in accordance with the present invention allows the frame means 2 to be repeatably and accurately fixed to the skull it is apparent that the apparatus can be removed from the patient's head following the imaging scan and can be refitted at a later time immediately prior to surgery. The inherent reproducibility of fit provided by the cast and the biassing means (i.e. the straps and headrest) ensure that the alignment error introduced by removal and refitting of the apparatus is minimal. In practise this error is believed to be less than 1 millimetre.

An alternative embodiment of the invention is shown in FIGS. 11, 12 and 13 in which corresponding reference numerals to those appearing in FIGS. 1 to 10 are used where appropriate.

In FIG. 11 an alternative support means 131 comprises a curved plate 136 formed of a composite plastics material (preferably glass fibre reinforced nylon material) having a generally arched configuration. The curved plate 136 is provided on each side with longitudinally extending vertical strips 137 and 138 in which are formed longitudinal slots 139 and 140 respectively.

A dental tray 141 is bonded to the curved plate 136 so as to be supported in the same general attitude as the cast 30 of the previous embodiment as shown in FIG. 3. The dental tray 141 is formed of similar material to that of the curved plate 136 and is provided with holes 142 distributed over its surface to assist in keying the acrylic impression material in place.

A cast (not shown) on the patient's teeth is formed by placing in the dental tray 141 a layer of an acrylic material in a pre-set state and taking an impression of the patient's upper teeth and/or palate as required. The material used in this example contains poly(ethylmethacrylate) powder and a monomer of tetrahydrofurfurylmethacrylate, with 2.5 percent v/v NN dimethyl paratoluidene. The dental tray 141 is then removed from the patient's mouth and the material allowed to set to provide a preformed cast. This material is non-exothermic, non-irritant to the patient and does not shrink on setting. An advantage of this method compared with that of the previous embodiment is that the cast can be formed in a single operation and the act of removal from the patient's teeth automatically provides clearance of the undercut of the teeth so that little or no finishing of the cast is required to ensure that the cast will subsequently be readily positionable within the mouth. A range of sizes of dental tray 141 are available to be incorporated in the support means 131 for example small, medium and large sizes.

The dental tray 141 comprises a U-shaped portion 143 having an upstanding peripheral wall 144 and an inner bridge portion 145 for projecting generally into proximity with a patient's palate for receiving that part of the layer which is to be indented with an impression of the patient's palate. A line of perforations 146 is provided peripherally of the bridge portion such that the bridge portion 145 can be readily removed by cutting or snap action prior to forming the cast in those cases where a patient's dentition is considered to be adequate to seat the cast without the need for a palate engaging bridge portion. Although the bridge portion 145 can be retained in such cases it does make speech difficult for the patient in use and for this reason it may be preferable to remove the bridge portion where possible. The bridge portion 145 would however be typically left in position where a patient had few upper teeth or no upper teeth at all.

The support means 131 further comprises modified location plates 147 which, unlike the location plates 45 and 46 of the previous embodiment as shown in FIG. 3, are adjustably connectable to the curved plate 136 by screw fittings 148. The screw fittings 148 comprise spaced apart vertical slots 149 and 150, an aluminium bracket 151 having threaded holes 152 and screws 153 which extend through the slots of the location plates through the horizontal slot 140 of the curved plate 136 and into threaded engagement with a hole 152 of the bracket 151. The location plates 147 are attachable one to each side of the curved plate 136 and are adjusted in position before tightening the screws 153 by means of an Allen key. Each location plate 147 is provided at its upper extremity with a flange 154 extending in a direction away from the plate 136 and is provided with screw holes 155.

During an initial positioning procedure the location plates 147 are screwed to the frame member 3 whilst the cast is presented to the mouth of the patient and is adjusted in position until it fits snugly against the upper teeth of the palate. When the frame 3 is suitably positioned the screws 153 are tightened and thereafter the relative position of the locating plates 147 and the curved plate 136 remains fixed.

Screws 156 provided for connecting the locating plates 147 to the frame 3 are provided with knurled heads so as to be fitted and removed by hand.

FIG. 12 shows an underneath view of the support means 131 of FIG. 11 after connection to a frame 3.

A side view of the support means 131 is also shown in FIG. 13 where additionally a modified headrest 113 is provided. The headrest 113 comprises a post 114 mounted so as to extend upwardly at right angles from the U-shaped bracket 8 which is slidably connected to the frame member 3 so as to be adjustable forwardly and rearwardly with respect to the patient's head. Screw clamps 17 and 18 enable the U-shaped bracket 8 to be locked in a required position and the arms 4 and 5 are calibrated by means of a scale 116 so that the post 114 can be repeatably positioned in the plane of the frame member.

The post 114 is arranged to adjustably support a tray 117 in which is moulded a silicone rubber pad 118 which is moulded to fit snugly against the rear (i.e. occiput) of the patient's head. The vertical position (i.e. at right angles to the plane of the frame member 3) of the tray 117 is adjustable and can be clamped into position by means of a screw clamp 119. The height of the tray is calibrated by a vertical scale 120 so that it can be repeatably positioned.

During an initial locating procedure the tray is filled with a pad 118 containing silicone rubber in an unset condition and the headrest 113 is adjusted so that the pad fits tightly against the patient's occiput and the headrest clamped into position whilst the material sets into a solid state. The horizontal and vertical positions of the headrest are recorded as a set of co-ordinates specific to that patient so that in subsequent fitting the headrest 113 can be precisely relocated relative to the frame member 3. Precise relocation of the headrest 113 is important in that it ensures that the cast is always biassed into correctly seating engagement with the teeth and/or palate. Any errors in the direction of bias might otherwise result in sufficient moment being applied to the cast to unseat and tilt the cast leading to incorrect positioning of the frame means 3.

The supporting strap 23 is connected to an upper end of the tray 117 so that after tightening of the straps the patient's head is engaged firmly by both the headrest 113 and by the cast within the patient's mouth. Using such an arrangement the use of ear plugs as previously described is not found to be required and the apparatus can be comfortably worn for extended periods of time.

It will be apparent that use of the apparatus in accordance with the present invention is not limited to use with the BRW stereotactic system and any other equivalent system can be used. In each case use is made of the constant relative position between the frame member and the patient's skull so that in effect the imaged co-ordinates are spatially defined with reference to the frame means and these co-ordinates are subsequently made use of for guiding surgical instruments.

The co-ordinates obtained from the imaging procedure are usable for directing the instrument even if the frame means 2 is removed from the patient's head following the imaging procedure provided the apparatus is refitted in precisely the same relative position to the skull immediately prior to the use of the stereotactic instrument.

The large number of contact points provided by the teeth and palate of the patient ensure that such relocation is achievable when refitting the cast 30. The large surface area over which the cast 30 makes contact with the patient also ensures stability and comfort in use.

Whilst individual teeth may be prone to small movement of the order of a fraction of a mm the upper dentition as a whole does not move relative to the skull so that the overall reproducability of fit is extremely good even when successive fittings are spaced apart by periods of several months.

In an alternative embodiment (not shown) the cast is moulded so as to make contact only with the patient's teeth. Such an arrangement might be appropriate for example where the patient had some abnormality of the palate. Alternatively in the case of a patient having few or no teeth at all the cast could be arranged to contact only the patient's palate.

Apparatus in accordance with the present invention can be easily fitted by relatively unskilled technicians and is suitable for out-patient use thereby avoiding the need for the admission of patient's requiring imaging or other diagnostic procedures.

As indicated above each patient will have an associated mouth piece assembly which can be stored between successive treatments in a relatively small space. This mouth piece assembly (together with the headrest and its alignment co-ordinates when using the apparatus of FIGS. 11 to 13) embodies a record of all necessary dimensional information specific to fitting the apparatus to that patient.

In an alternative embodiment the apparatus shown in any of FIGS. 1 to 10 is modified to include a cushion which is an empty sack which is inflatable with gas or liquid after positioning of the headrest. This enables the headrest load to be distributed for patient comfort.

In an alternative embodiment the frame means is of anodised aluminium.

What is claimed is:

1. Apparatus for use in stereotactic diagnosis and treatment comprising frame means and fixation means for repeatably and reproducibly fixing the frame means to the patient's head such that locations within the head are spatially definable with reference to the frame means, characterised in that the fixation means comprises a cast of the patient's upper teeth and or palate, the cast including a U-shaped portion indented with an impression of substantially all of the patient's upper teeth;

support means positioned with the fixation means for rigidly connecting the cast to the frame means, the support means including a plate having a central portion connected to the front of the cast so as to be generally coplanar with the U-shaped portion and which extends rearwardly inside of the patient's mouth in supporting contact with the cast to at least as far as the location of the premolar teeth, the plate further including side portions which extend rearwardly outside of the patient's mouth to at least as far as the location of the premolar teeth and at a downwardly inclined angle with respect to the central portion of the plate; and biasing means non-invasively engageable with the head and operable between the head and the frame means and/or the fixation means to bias the cast into positive contact with the upper teeth and or palate.

2. Apparatus as claimed in claim 1 wherein the cast has a contact surface which in use engages in intimate contact the inner and inferior aspects of substantially all of the patient's upper teeth.

3. Apparatus as claimed in claim 2 wherein the contact surface further engages the outer aspect of the molar and premolar teeth.

4. Apparatus as claimed in any of claims 2 to 3 wherein the cast includes a bridge portion (33) conforming to the palate and forming a continuous bridge between the arms or the U-shaped portion.

5. Apparatus as claimed in claim 1 wherein the support means includes a tray connected to the plate and the cast is formed from a layer of a material which is initially indentable so as to take an impression of the patient's upper teeth and/or palate and which subsequently cures to a rigid form retaining the impression formed therein.

6. Apparatus as claimed in claim 1 including demountable connecting means operable between the fixation means and the frame means.

7. Apparatus as claimed in claim 6 wherein the support means include vertical location plates connected to the side portions thereof and having screw fittings operable between the location plates and the frame means.

8. Apparatus as claimed in claim 7 wherein the side portions are fixed to the location plates after an initial positioning procedure during which the frame means is supported at a desired position about the patient's head and the corresponding relative positions of the side portions and the location plates are recorded.

9. Apparatus as claimed in claim 8 wherein the side portions are fixed to the location plates by screw fittings.

10. Apparatus as claimed in claim 9 including positioning arc means detachably connectable to the frame means and defining a working space relative to the frame means which is equal to or less than the corresponding working space required by stereotatic instruments or the like which are to be subsequently fitted to the frame means in use whereby the initial positioning procedure carried out with the arc so connected ensures the frame means is positioned relative to the head so as to maintain working clearance between the head and any such instrument.

* * * * *